US005674474A

United States Patent [19]
Fisher et al.

[11] Patent Number: 5,674,474
[45] Date of Patent: Oct. 7, 1997

[54] SNF 2 GEL OF IMPROVED STAND-UP AND STABILITY

[75] Inventors: Steven W. Fisher, Middlesex; Shannon K. Campbell, Piscataway; Edward A. Tavss, Kendall Park; Marilou T. Joziak, South River, all of N.J.

[73] Assignee: Colgate Palmolive Company, New York, N.Y.

[21] Appl. No.: 597,772

[22] Filed: Feb. 7, 1996

Related U.S. Application Data

[63] Continuation-in-part of Ser. No. 200,034, Apr. 25, 1994.

[51] Int. Cl.$^6$ ............................. A61K 7/18; A61K 33/16
[52] U.S. Cl. ............................................. 424/52; 424/673
[58] Field of Search ................................ 424/52, 673

[56] References Cited

U.S. PATENT DOCUMENTS

| | | | |
|---|---|---|---|
| 4,374,823 | 2/1983 | Harvey et al. | 424/52 |
| 4,540,576 | 9/1985 | Zahradnik | 424/52 |
| 4,770,634 | 9/1988 | Pellico I | 424/52 |
| 5,071,638 | 12/1991 | Yoshie et al. | 424/49 |
| 5,073,363 | 12/1991 | Pellico II | 424/52 |
| 5,094,841 | 3/1992 | Pine | 424/52 |

*Primary Examiner*—Shep Rose
*Attorney, Agent, or Firm*—Paul Shapiro

[57] ABSTRACT

A $SnF_2$ gel composition exhibiting improved stand-up and stability to exposure to air containing moisture which composition contains $SNF_2$, anhydrous glycerin, a polyethylene glycol having an average molecular weight of 1000 and xanthan gum.

10 Claims, No Drawings

SNF 2 GEL OF IMPROVED STAND-UP AND STABILITY

This is a continuation-in-part of application Ser. No. 08/200,034 filed Apr. 25, 1994.

BACKGROUND OF THE INVENTION

1. Field of the Invention

This invention relates to a stannous fluoride dental gel having improved cosmetic stability to air and moisture.

2. The Prior Art

Stannous fluoride ($SnF_2$) has been reported to be an effective agent for treating various oral conditions. Included in the dental benefits imparted by $SnF_2$ is the reduction of dental caries. The anticaries benefit has been attributed to the fluoride ion component of the $SnF_2$ salt.

$SnF_2$ has also been indicated clinically to be efficacious in the reduction of dentinal hypersensitivity. This latter therapeutic effect is believed to be attributable, to a large degree, to the stannous ion ($Sn^{2+}$) component of the salt.

In order for $Sn^{2+}$ to be efficacious it must be stable and freely available and not be in chemical combination with other ingredients. Stannous fluoride as a 0.4% by weight $SnF_2$ preparation has most frequently been demonstrated to be the concentration of choice in the treatment of dental caries and dentine hypersensitivity.

Due to the chemical instability of stannous fluoride in aqueous solutions, the fluoride salt is normally applied to the teeth as a nonaqueous gel wherein anhydrous glycerin is a carrier for the $SnF_2$ salt. $SnF_2$ in the form of a solution in anhydrous glycerin is presently provided to the professional for use as a topical treatment in the dental office. The professional dilutes this formulation with an aqueous solution immediately prior to application to the teeth.

While topical applications are frequently performed in the dental office there is also a need for follow-up daily application and use by the patient. Thus, "home-care" or "patient-care" availability is desirable. For this purpose a gel with the requisite physical properties to accommodate toothbrush application is the desired marketable form. Unfortunately, $SnF_2$ dissolved in anhydrous glycerin, the form found most suitable for preserving the chemical stability of $SnF_2$, does not lend itself to application with a toothbrush. For example, U.S. Pat. Nos. 4,418,057 and 4,533,544 disclose topical preparations of 0.40% $SnF_2$ which are chemically stable when suspended in anhydrous glycerin thickened with hydroxyethylcellulose. A drawback to these gel preparations is that the gels have a semi-liquid consistency, and when dispensed on the bristles of a toothbrush, the get immediately sinks through the bristles and runs off the brush so that only a relatively small portion of the dispensed product is retained on the toothbrush. Consequently, $SnF_2$ suspended in hydroxyethylcellulose thickened anhydrous glycerin has found limited acceptability as a home-care product as the semi-fluid gel composition cannot be controllably retained on the surface of toothbrush bristles and then applied to teeth to reliably supply $SnF_2$ for the treatment of dental caries or dentine hypersensitivity.

To preclude the erratic, inconsistent applications of $SnF_2$ encountered with the $SnF_2$ semi-liquid gels of the prior art, there is disclosed in copending patent application Ser. No. 08/200,034, a $SnF_2$ gel preparation formulated with a polyethylene glycol having an average molecular weight of 1000 ("polyethylene glycol 1000") that has improved "stand-up" properties, i.e., the gel has an extrudable consistency such that extruded ribbons of the gel, when dispensed onto the bristles of a toothbrush, will stand-up on the top surface of the bristles for a time sufficient to allow full application to the teeth, e.g., a time interval of at least 0.5–1.0 minute.

A drawback to the $SnF_2$ gel disclosed in Ser. No. 08/200,034 is encountered during storage or use, as the gel, due to the hygroscopic nature of the polyethylene glycol 1000 present to enhance stand-up, deliquesces upon exposure to air containing moisture which substantially destroys its stand-up property, degrading the gel to a semi-liquid consistency whereby the gel is unsuitable for home care usage.

Liquefaction of the gel of Ser. No. 08/200,034 has been observed when the product is in contact to air containing moisture for a period of time as short as one minute. Liquefaction becomes a serious problem when the cap to the orifice of the tube or pump in which the gel is packaged is allowed to remain open by the user causing a cosmetically unacceptable liquefaction of the gel ingredients with the result that the gel product will drip out of the tube or pump prior to use.

SUMMARY OF THE INVENTION

In accordance with the present invention there is provided a chemically and cosmetically stable stannous fluoride gel that has stand-up properties suitable for tooth brush applications and does not undergo liquefaction when exposed to air containing moisture wherein the composition is comprised of $SnF_2$, anhydrous glycerin, a polyethylene glycol thickener having an average molecular weight of 1000 and a small amount of xanthan gum effective to inhibit liquefaction of the gel.

DESCRIPTION OF THE PREFERRED EMBODIMENTS

The $SnF_2$ gel compositions of the present invention are generally comprised of about 0.30 to about 1.0% by weight $SnF_2$ and preferably about 0.35 to about 0.90% by weight; about 87 to about 99% by weight anhydrous glycerin and preferably about 90 to about 95% by weight and about 3.0 to about 10.0% by weight of a polyethylene glycol thickening agent having an average molecular weight of 1000 and preferably about 5.0 to about 8.0% by weight and about 0.01 to about 0.5% of a xanthan gum and preferably about 0.2 to about 0.4% by weight. The polyethylene glycol used in the practice of the present invention is a nonionic polymer of ethylene oxide having an average molecular weight of 1000 and the general formula

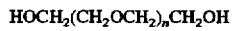

$$HOCH_2(CH_2OCH_2)_nCH_2OH$$

wherein n represents the average number of oxyethylene groups, such polyethylene glycol being designated hereinafter as polyethylene glycol 1000, the number 1000 representing the average molecular weight.

It is essential to the practice of the present invention to use xanthan gum to inhibit liquefaction of the $SnF_2$ gel. Xanthan gum is known in the art and has been proposed for use in dentifrice compositions in U.S. Pat. No. 4,401,648. Xanthan gum is a fermentation product prepared by action of the bacteria of the genus Xanthomonas upon carbohydrates. Four species of Xanthomonas, namely, *X. campetris*, *S. phaseoli*, *X. malvocearum* and *X. carotae* are reported in the literature to be the most efficient gum producers. Although the exact structure is not determined, it is generally accepted to be a heteropolysaccharide with a molecular weight of several million and contains D-glucose, D-mannose, and D-glucoronic acid in molar ratio of 2.8:3:2.0. The molecule contains 4.7% acetyl and about 3% pyruvate. The proposed chemical structure configuration can be found in McNeely and Kang, Industrial gums, ed. R. L. Whistler, Ch. XXI, 2nd Edition, New York, 1973. The procedure for growing, isolating and purifying the xanthan gum is found in Manufacturing Chemist, May 1960, pages 206–208 (including mention at page 208 of potential use of gums therein described for formulating toothpastes).

Xanthan gum is incorporated in the $SnF_2$ gel composition of the present invention in an amount of about 0.01 to 0.5% by weight and preferably about 0.2 to about 0.4% by weight. It has been found necessary to use xanthan gum as a liquefaction inhibitor in order to provide a stable, semi-solid, extrudable dentifrice which undergoes substantially no liquefaction upon exposure to air containing moisture for extended time periods. As will hereinafter be demonstrated, other gums commonly used in as dentifrice formulations such as hydroxyethyl cellulose, iota carrageenan, carboxymethyl cellulose and Carbopol, a crosslinked acrylic acid copolymer, have been found to be substantially inoperative in preventing liquefaction of the $SnF_2$ gel formulated using a polyethylene glycol 1000 thickener upon exposure to air containing moisture with the result that a cosmetically unacceptable product is produced which lacks the rheological properties required for an a stable dentifrice.

Also included in the compositions of the present invention is an effective flavoring amount of a flavor compatible and stable with the stannous fluoride salt. The flavor ingredient constitutes about 0.05 to about 1% by weight and preferably about 0.1 to about 0.9% by weight of the gel composition. Suitable flavoring constituents are flavoring oils, e.g. oils of spearmint, peppermint, wintergreen, clove, methyl salicylate and menthol.

The $SnF_2$ dental gel of this invention may be prepared by suspending $SnF_2$, predissolved in anhydrous glycerin, flavor, polyethylene glycol 1000 and the xanthan gum in anhydrous glycerin heated to a temperature of 35° to 140° C. by mixing in any suitable mixer, such as a Lightening mixer for about 30 minutes until a homogenous solution is formed. A substantially rigid, non-fluid gel product is obtained upon cooling. The final product may be packaged in any suitable container compatible with $SnF_2$ gels such as plastic or laminate tubes or bottles.

The $SnF_2$ gel product of the present invention undergoes virtually no liquefaction when exposed to air containing moisture for extended time periods and has an extrudable consistency and upon being extruded as a ribbon onto the bristles of a toothbrush, the ribbon remains in a stand-up position on the toothbrush without substantially sinking through the bristles for at least two minutes.

The following example is further illustrative of the present invention, but it is understood that the invention is not limited thereto. All amounts and proportions referred to herein and the appended claims are by weight.

EXAMPLE

A $SnF_2$ gel of the present invention was prepared with the following ingredients:

| Ingredient | Concentration (wt %) |
| --- | --- |
| Glycerin | 92.800 |
| Polyethylene Glycol 1000 | 6.00 |
| $SnF_2$ | 0.4000 |
| Xanthan Gum | 0.300 |
| Flavor | 0.5000 |

The glycerin, flavor, xanthan gum and polyethylene glycol 1000 were premixed at 100° C. for 30 minutes to form a homogenous solution. The solution was then mixed with $SnF_2$ predissolved in glycerin for 30 minutes at a speed of 800 revolutions/min. with a Lightning mixer. When cool, the resultant gel was of extrudable consistency, cosmetically attractive and was tubed in plastic laminate tubes. When a ribbon of the gel was extruded onto the bristles of a toothbrush, the ribbon remained firm and did not significantly sink through the bristles for at least 2 minutes.

To determine the stability of the gel to moisture, 10 grams of the gel were placed in a pre-weighed, two ounce ointment jar to which was added 0.4 milliliters water. The jar was sealed with a screw-on cap and stored for 4 days at 23° C. After the 4 day storage period, the jar was opened and inverted for one minute to allow any liquid to drain off. Thereafter the jar was reweighed to determine the loss in grams, if any, of the gel, such loss in grams being representative of the degree of liquefaction of the gel. The results of the liquefaction study are recorded in the Table below.

For purposes of comparison, the procedure of the example was repeated except gums other than xanthan gum were substituted for xanthan in preparing the gels. The liquefaction results obtained with these comparative gums are also recorded in the Table below.

TABLE

| Dental Gel | Gum | Wt. % Gum | PEG 1000 (Wt. %) | Glycerin (Wt. %) | $SnF_2$ (Wt. %) | Flavor (Wt. %) | Weight Loss (grams) | % Gel Loss |
| --- | --- | --- | --- | --- | --- | --- | --- | --- |
| A | Xanthan | 0.3 | 6 | 92.80 | 0.4 | 0.5 | 0.00 | 0.00 |
| B | HEC* | 0.31 | 6 | 92.80 | 0.4 | 0.5 | 2.80 | 28.0 |
| C | HEC | 0.41 | 6 | 92.80 | 0.4 | 0.5 | 1.68 | 16.8 |
| D | CMC** | 0.5 | 6 | 92.80 | 0.4 | 0.5 | 1.96 | 19.6 |
| E | Carbopol | 0.25 | 6 | 92.80 | 0.4 | 0.5 | 2.52 | 25.2 |
| F | None | 0 | 7 | 92.10 | 0.4 | 0.5 | 5.33 | 53.3 |

*HEC — Hydroxyethylcellulose
**CMC — Carboxymethylcellulose

The % gel loss results recorded in the Table above indicate that only the composition of the Example, Dental Gel A containing xanthan gum exhibited acceptable stability wherein no gel loss occurred during the 4 day exposure to moisture, whereas the comparative compositions which contained a gum other than xanthan, encountered gel losses of 16.8–53.3%.

What is claimed is:

1. A stannous fluoride anhydrous gel composition exhibiting improved stand-up and stability when exposed to air containing moisture which comprises $SnF_2$, anhydrous glycerin, a polyethylene glycol having an average molecular weight of about 1000 and xanthan gum.

2. The composition of claim 1 wherein $SnF_2$ is present in the composition at a concentration of about 0.30 to about 1.8% by weight.

3. The composition of claim 1 wherein anhydrous glycerin is present in the composition at a concentration of about 87 to about 97% by weight.

4. The composition of claim 1 wherein the polyethylene glycol is present in the composition at a concentration of about 3.0 to about 10% by weight.

5. The composition of claim 1 wherein the xanthan gum is present in the composition at a concentration of about 0.01 to about 0.5% by weight.

6. In a method for preparing a stable anhydrous gel formulated with $SnF_2$, anhydrous glycerin and polyethylene glycol 1000, the improvement which comprises incorporating in the composition about 0.01 to about 0.5% by weight of a xanthan gum whereby liquefaction of the gel is inhibited when exposed to air containing moisture.

7. The method of claim 6 wherein the xanthan gum is present in the composition at a concentration of about 0.2 to about 0.4% by weight.

8. The method of claim 6 wherein $SnF_2$ is present in the composition at a concentration of about 0.30 to about 1.8% by weight.

9. The method of claim 6 wherein anhydrous glycerin is present in the composition at a concentration of about 87 to abut 97% by weight.

10. The method of claim 6 wherein the polyethylene glycol is present in the composition at a concentration of about 3.0 to about 10% by weight.

* * * * *